(12) United States Patent
Rose-Fricker et al.

(10) Patent No.: US 6,372,966 B1
(45) Date of Patent: Apr. 16, 2002

(54) KENTUCKY BLUEGRASS VARIETY KNOWN AS 'BRILLIANT'

(75) Inventors: Crystal Rose-Fricker, Canby, OR (US); William A. Meyer, Colts Neck, NJ (US)

(73) Assignee: Pure Seed Testing Inc., Canby, OR (US)

( * ) Notice: Subject to any disclaimer, the term of this patent is extended or adjusted under 35 U.S.C. 154(b) by 0 days.

(21) Appl. No.: 09/589,521

(22) Filed: Jun. 7, 2000

(51) Int. Cl.[7] .............................. A01H 5/00; A01H 1/00; A01B 79/00
(52) U.S. Cl. .................. 800/298; 800/260; 47/58.1
(58) Field of Search ................................ 800/298, 388, 800/260; 47/58.1

(56) References Cited

FOREIGN PATENT DOCUMENTS

| WO | WO 92/04449 | 3/1992 |
| WO | wo 92/11764 | 7/1992 |

OTHER PUBLICATIONS

Harrington et al., "Tolerance to Nerbicides of Ground Cover Species for New Zealand Orchards," *Plant Protection Quarterly* 13:111–116 (1998).
Comes et al., "Differential Response to Glyphosate and Growth Patterns of Red Fescue Fescue–Rubra." *J. Aquatic Plant Management* 23:32–35 (1985) Abstract.
Turf–Seed, Inc., Pure Seed Testing, Inc., *Field Day 17*, Jun. 15, 1999, Front cover and p. 10.
Turf–Seed, Inc., Pure Seed Testing, Inc., *Field Day 18*, Jun. 15,2000, pp. 1–148.
Turf–Seed, Inc., Pure Seed Testing, Inc., *Field Day 14*, Jun. 20, 1996, Front cover and p. 32.
Declaration from Crystal Rose–Fricker executed on Oct. 16, 2000.

*Primary Examiner*—Bruce R. Campbell
*Assistant Examiner*—Annette H. Para
(74) *Attorney, Agent, or Firm*—Klarquist Sparkman LLP

(57) ABSTRACT

A Kentucky bluegrass variety known as 'Brilliant' (experimental code PST-B2-42), and seed used to produce the grass are provided. Methods of using the grass plant and the seed are also provided. This grass is particularly suitable for use in lawns, golf courses, sod, and other turfs where excellent turf quality is desired.

33 Claims, No Drawings

KENTUCKY BLUEGRASS VARIETY KNOWN AS 'BRILLIANT'

BACKGROUND OF THE INVENTION

Kentucky bluegrass (*Poa pratensis* L.) is a short- to medium height, cool-season, perennial grass that has smooth, soft, green to dark green leaves with boat-shaped tips. It grows best during cool, moist weather on well-drained, fertile soils with a pH between 6 and 7 and spreads via rhizomes to form a dense sod. Historically, Kentucky bluegrass has been important for use in agriculture in the North Central and Northeastern regions of the United States. This is because Kentucky bluegrass tolerates close and frequent grazing or mowing better than other cool-season grasses. This ability makes Kentucky bluegrass and ideal species in permanent pastures, as well as in turf situations (e.g., lawns, parks, sod production, and athletic fields).

More recently, Kentucky bluegrass has become an important turf grass in part because its rhizomes form a dense sod, which also makes it ideal for erosion control, particularly in grass waterways.

SUMMARY OF THE INVENTION

The inventor has produced a Kentucky bluegrass variety termed 'Brilliant' (experimental code PST-B2-42) that is different from all known varieties of Kentucky bluegrass. Particularly, mature 'Brilliant' (PST-B2-42) plants reach a height from about 36 cm to about 63 cm tall, have a narrow tiller leaf width of from about 2 mm to about 4 mm, and a high turf quality rating.

At least 2500 seeds of 'Brilliant' (PST-B2-42) have been deposited with the ATCC. Therefore, these seeds are known and readily available to the public.

In one embodiment, the invention provides Kentucky bluegrass plants having the morphological and physiological characteristics of PST-B2-42, as well as seeds of such plants. In another embodiment, the invention provides grass plants having the genotype of PST-B2-42. The invention also encompasses Kentucky bluegrass plants that are produced by crossing PST-B2-42 with other grass varieties, as well as seeds of such plants. In another aspect, the invention provides a method of producing grass seed, comprising planting seed from PST-B2-42 under conditions that result in the germination of the seed, growth of grass plants and setting of progeny seed, and then harvesting the progeny seed.

These and other aspects of the invention will become more apparent from the following description.

DESCRIPTION OF THE INVENTION

Seed Deposits, Description of Plants

Seeds of the Kentucky bluegrass variety termed 'Brilliant' (experimental code PST-B2-42) were deposited with the Ameican Type Culture Collection (ATCC, Manassas, Va.) on Aug. 18, 2000, under accession number PTA-2401. The variety is also maintained at, and available from, Pure Seed Testing, Inc., P.O Box 449, Hubbard, Oreg. 97032.

The following growth characteristics were observed for 'Brilliant' (PST-B2-42) plants that were approximately one to two years old, grown in space plants or seeded rows near Hubbard, Oreg. Variations on these measurements may be observed for plants of differing ages, grown in other locations and/or under different prevailing weather conditions.

TABLE 1

1997 mean morphological measurements for entries on a Kentucky bluegrass Plant Variety Protection (PVP) trial planted fall of 1995 near Hubbard, Oregon

| ENTRY | PLANT HEIGHT (cm) | TILLER LEAF WIDTH (mm) |
|---|---|---|
| 'Brilliant' (PST-B2-42) | 48.48 | 2.36 |
| 'Unique' | 55.29 | 3.20 |
| 'Baron' | 43.46 | 2.70 |
| L.S.D. (0.05)* | 2.85 | 0.29 |

*To determine statistical differences among entries, subtract one entry's mean from another entry's mean. Statistical differences occur when this value is equal to or larger than the corresponding L.S.D. value.

TABLE 2

1998 mean morphological measurements for entries on a Kentucky bluegrass seed yield trial seeded fall of 1997 near Hubbard, Oregon

| ENTRY | PLANT HEIGHT (cm) | TILLER LEAF WIDTH (mm) |
|---|---|---|
| 'Brilliant' (PST-B2-42) | 46.98 | 3.08 |
| 'Unique' | 76.89 | 3.74 |
| 'Baron' | 54.76 | 3.95 |
| L.S.D. (0.05) | 2.42 | 0.23 |

TABLE 3

National Turf Evaluation Program (NTEP) Mean Turfgrass Quality Ratings of Kentucky bluegrass Cultivars Grown under Medium/High Input at Eight Locations using a 0.5–1.0 inch Mowing Height
1997 Data
Turfgrass Quality Ratings 1–9; 9 = Ideal Turf

| ENTRY | MEAN |
|---|---|
| 'Brilliant' (PST-B2-42) | 6.7 |
| 'Unique' | 6.3 |
| 'Baron' | 5.3 |
| L.S.D. (0.05) | 0.3 |

TABLE 4

1997 mean morphological measurements for entries in a Kentucky bluegrass PVP trial planted fall of 1995 near Hubbard, Oregon

| ENTRY | TILLER LEAF LENGTH (cm) | BRANCHES AT LOWEST WHORL (#) |
|---|---|---|
| 'Brilliant' (PST-B2-42) | 7.95 | 3.8 |
| 'Unique' | 6.63 | 4.2 |
| 'Baron' | 7.34 | 4.7 |
| L.S.D. (0.05) | 0.83 | 0.3 |

TABLE 5

NTEP Billbug Ratings of Kentucky bluegrass Cultivars Grown Under Medium/High Input 1997 Data
Billbag Ratings 1–9; 9 = No Damage

| ENTRY | MEAN |
|---|---|
| 'Brilliant' (PST-B2-42) | 8.0 |
| 'Unique' | 7.0 |
| 'Baron' | 6.0 |
| L.S.D. (0.05) | 1.2 |

TABLE 6

NTEP Stemminess Ratings of Kentucky bluegrass Cultivars Grown under
Medium/High Input 1997 Data
Stemminess Ratings 1–9; 9 = Least Stemminess

| ENTRY | MEAN |
|---|---|
| 'Brilliant' (PST-B2-42) | 8.0 |
| 'Unique' | 8.0 |
| 'Baron' | 4.0 |
| L.S.D. (0.05) | 1.9 |

TABLE 7

NTEP Leaf Texture Ratings of Kentucky bluegrass Cultivars Grown under
Medium/High Input 1997 Data
Leaf Texture Ratings 1–9; 9 = Very Fine

| ENTRY | MEAN |
|---|---|
| 'Brilliant' (PST-B2-42) | 6.4 |
| 'Unique' | 6.3 |
| 'Baron' | 5.3 |
| L.S.D. (0.05) | 0.2 |

TABLE 8

NTEP Genetic Color Ratings of Kentucky bluegrass Cultivars Grown
under Medium/High Input 1997 Data
Genetic Color Ratings 1–9; 9 = Dark Green

| ENTRY | MEAN |
|---|---|
| 'Brilliant' (PST-B2-42) | 6.4 |
| 'Unique' | 6.4 |
| 'Baron' | 6.3 |
| L.S.D. (0.05) | 0.2 |

TABLE 9

NTEP Mean Turfgrass Quality Ratings of Kentucky bluegrass Cultivars
Grown under Medium/High Input at Sixteen Locations in the Cool-Humid
Zone 1997 Data
Turfgrass Quality Ratings 1–9; 9 = Ideal Turf

| ENTRY | MEAN |
|---|---|
| 'Brilliant' (PST-B2-42) | 6.8 |
| 'Unique' | 6.4 |
| 'Baron' | 5.8 |
| L.S.D. (0.05) | 0.2 |

TABLE 10

NTEP Powdery Mildew (Greenhouse Study) Ratings of Kentucky
bluegrass Cultivars Grown Under Medium/High Input 1997 Data
Powdery Mildew Ratings 1–9; 9 = No Disease

| ENTRY | MEAN |
|---|---|
| 'Brilliant' (PST-B2-42) | 9.0 |
| 'Unique' | 9.0 |
| 'Baron' | 2.0 |
| L.S.D. (0.05) | 1.1 |

Producing the Kentucky Bluegrass Variety Termed 'Brilliant'

The 'Brilliant' variety of Kentucky bluegrass (*Poa pratensis* L.) was developed at Pure Seed Testing, Inc. of Hubbard, Oreg. The 'Brilliant' variety originated as a single highly apomictic plant selected from the progeny of a cross between the Kentucky bluegrass variety 'Unique' and either the Kentucky bluegrass variety 'Rita' or the variety 'C-727.'

'Unique', the maternal parent, was selected from an old turf area in Exter, R.I. in 1987 (Rose-Fricker et al., *Crop Sci.* 39:290,1999). 'Unique' has good resistance to stripe smut (caused by *Ustilago striiformis* (Westend) Neisel.) and leaf spot (caused by *Drechlera poae* (Baudys) Shoem.), a medium green color, compact growth habit and good turf performance.

'Rita', a possible paternal parent of 'Brilliant', originated as a single apomictic clone collected from an old turf area in Denver, Colo., in the spring of 1986. 'Rita', has a dark blue color, aggressive growth habit and good overall disease resistance.

'C-727,' the other possible paternal parent, was originally collected from a cemetery in St. Johnsbery, Vt. 'C-727' has good seed yield potential.

Plants of 'Unique', 'Rita' and 'C-27' varieties were brought into a greenhouse from spaced-plant nurseries in Oregon during the spring of 1991 and crossed. Seedlings from this cross were established in a field nursery in Oregon during the fall of 1991. Promising hybrids were identified during May and June of 1992. The 'Brilliant' variety was selected and given the experimental code PST-B2-42. Floret fertility (seed set) was evaluated by rubbing seed stripped from panicles to test good seed size and fill. PST-B2-42 seed was harvested and used to establish single plant progeny turf plots in Oregon and at Rutgers University in New Jersey. During 1993 and 1994, PST-B2-42 was evaluated for seed yield and turf performance. A breeder seed nursery consisting of 585 plants of PST-B2-42 was established during the fall 1994 in Oregon. PST-B2-42 is a facultative apomict, approximately 95% percent of its progeny appearing genetically identical to the maternal parent. Aberrant, off-type and variant plants were removed from the breeder seed nursery leaving 432 plants.

PST-B2-42 is a stable and uniform variety. Breeder seed is maintained by Pure Seed Testing, Inc. Seed propagation is limited to three generations of increase from breeder seed. The first generation is foundation, the second is registered, and the third is certified. No off-types or variants have been observed in the reproduction or multiplication of PST-B2-42. PST-B2-42 has produced turf of good quality and uniformity.

Production of the Kentucky Bluegrass Variety 'Brilliant' (PST-B2-42)

PST-B2-42 Kentucky bluegrass can be grown under normal conditions for growing turf grasses, and bulk seed for large-scale planting can be obtained by methods known in certified seed production. For example, bulk seed may be produced by planting PST-B2-42 seeds obtained from either ATCC or Pure Seed Testing, Inc., allowing the mature plants to produce seed by apomixis or cross-pollination with each other and then collecting the seed. Standard precautions should be taken to prevent cross-pollination from other grasses, such as growing the variety in an isolated plot of sterilized soil, removing adjacent vegetation, etc. The PST-B2-42 seeds deposited with ATCC are breeder seeds; propagation of plants from these seeds should preferably be performed under the conditions specified in the 1999 Oregon Certified Seed Handbook, published by Oregon State University Extension Service, Corvallis, Oreg. 97331, herein incorporated by reference.

The 'Brilliant' variety can also be asexually repoduced via propagules. Vegetative propagules: As used herein, the term vegetative propagules means sprigs, plugs, stolons and sod. Exemplary Uses of Kentucky Bluegrass Variety 'Brilliant' (PST-B2-42)

The Kentucky bluegrass PST-B2-42 is useful for planting in a variety of different environments. For example, the Kentucky bluegrass variety is useful for planting on steep slopes where soil erosion is likely to occur.

The Kentucky bluegrass PST-B2-42 is also useful in part because of its overall disease resistance, its narrow tiller leaf width and its high turf rating. These features render 'Brilliant' especially useful for sod production, athletic fields, golf course fairways, golf course roughs, parks, home lawns, and for with other varieties of Kentucky bluegrass seed. 'Brilliant' can also be used in mixtures with perennial ryegrass, tall fescue or fine fescue varieties. Thus, the 'Brilliant' variety (PST-B2-42) is especially marketable and therefore useful.

Molecular Characterization of the Kentucky Bluegrass Variety 'Brilliant'

The protein from three different Kentucky bluegrass varieties was tested to identify and compare various banding patterns. These varieties were 'Brilliant' (PST-B2-42), 'America', and 'Unique'.

Total protein banding patterns were visualized on two different isoelectric focusing gels. The first gel was at pH 3–7 and the second gel was at pH 3–10. The total protein-banding pattern was then visualized via silver staining.

The banding patterns of esterase (EST), phospohexose isomerase (PHI), and peroxidase (PER) were visualized on two different isoelectric focusing gels. The esterase and peroxidase enzymes were run on gels at pH 3–10, and the phosphohexose isomerase and esterase were run on gels at pH 3–7.

1. Results

The results from the peroxidase enzyme assay showed that 'Brilliant' had a different banding pattern than 'Unique' and 'America'.

The results from the esterase #1 and #2 enzyme assay showed that 'Brilliant', 'Unique' and 'America' varieties expressed different banding patterns from each other.

The results from the phosphohexose isomerase enzyme assay showed that all of the varieties had a similar banding pattern.

The results from the total protein assay, run on the isoelectric focusing gel (pH 3–7), showed that 'Brilliant' had a different banding patterns than 'Unique' and 'America'.

The results from the total protein assay, run on the isoelectric focusing gel (pH 3–10), showed that all of the varieties had a similar banding pattern.

Table 11 provided below provides a summary of the above-described results.

The electrophoretic analysis was conducted by HyPure® (part of Perkin Elmer Life Sciences), 3985 Eastern Road, Norton, Ohio 44203, U.S.A.

TABLE 11

Compilation of Results form Protein Analysis

| Variety Name | Silver Stain (pH 3–10) HyPure Gel VG-1040 | Silver Stain (pH 3–7) HyPure Gel FS-5080 | PHI HyPure Gel FS-5080 | #1 HyPure Gel VG-1040 | #2 HyPure Gel FS-5480 | PER HyPure Gel FS-5480 |
|---|---|---|---|---|---|---|
| 'Brilliant' PST-B2-42 | A | A | A | A | A | A |
| 'AMERICA' | A | B | A | B | B | B |
| 'UNIQUE' | A | B | A | C | C | B |

*A different letter was designated for each different banding pattern observed.

2. Methods

Three bulk samples were prepared for each type of test. The samples were prepared by grinding the seeds in a coffee grinder and then weighing out 800 mg for each test. For the enzyme assays 700 µL of a phosphate extraction solution was used per 200 mg crushed seed. For the total protein assays 700 µL of a 15% tetramethylurea and 20% ethylene glycol extraction solution was used per 200 mg crushed seed. The samples were incubated overnight at 4–8° C. and were then centrifuged the next morning. The resulting supernatant was then ready for the running out on the isoelectric focusing gels.

The isoelectric focusing gels ran for 80 minutes and were then immediately placed into their corresponding stains. When the electrophoresis banding patterns reached desired intensity the reaction was stopped and the gels were washed in water. The gels were then air dried and ready for the interpretation.

Introducing Traits of Kentucky Bluegrass Variety 'Brilliant' Into Other Grass Varieties The morphological and physiological characteristics of the 'Brilliant' variety of Kentucky bluegrass may be introduced into other grass varieties by conventional breeding techniques. For example, the 'Brilliant' variety may be grown in pollination proximity to another variety of Kentucky bluegrass, allowing cross-pollination to occur between the 'Brilliant' variety and the other variety, and then harvesting the hybrid seeds. Plants grown from these hybrid seeds can then be tested for the maintenance of the molecular characteristics described above for the 'Brilliant' variety, and/or the plants can simply be observed to see if they display the same growth characteristics described in the above tables.

In certain embodiments, the present invention contemplates the transformation of cells derived from the 'Brilliant' variety with one or more advantageous transgenes. Transgenes that confer resistance to herbicides, insect, disease (viral, bacterial, fungal, nematode) or drought resistance, standability, prolificacy, salt damage resistance, and quality are particularly useful. Examples of such genes and methods of transforming plants are described in U.S. Pat. No. 6,025,545 to Lundquist, et al., which is herein incorporated by reference.

Having illustrated and described the principles of the invention in multiple embodiments and examples, it should be apparent to those skilled in the art that the invention can be modified in arrangement and detail without departing from such principles. The invention, therefore, encompasses all modifications coming within the spirit and scope of the following claims.

What is claimed is:

1. A Kentucky bluegrass plant, comprising the morphological and physiological properties of a grass plant grown from the seed deposited under American Type Culture Collection No. PTA-2401.

2. Sod, comprising the grass plant of claim 1.

3. The grass plant of claim 1 planted in a golf course fairway.

4. The grass plant of claim 1 planted in a golf course rough.

5. The grass plant of claim 1 planted in a lawn.

6. The grass plant of claim 1 planted in an athletic field.

7. The grass plant of claim 1 planted in a park.

8. Progeny of a grass plant according to claim 1.

9. Seed of the grass plant of claim 1.

10. A seed mixture, comprising the seed of claim 9.

11. A vegetative sprig or clone of the grass plant of claim 1.

12. The grass plant of claim 1, further comprising at least one transgene.

13. Seed resulting from crossing the grass plant of claim 1 with a second grass plant.

14. A grass plant grown from the seed of claim 13.

15. Sod, comprising the grass plant of claim 14.

16. The grass plant of claim 14 planted in a golf course fairway.

17. The grass plant of claim 14 planted in a golf course rough.

18. The grass plant of claim 14 planted in a lawn.

19. The grass plant of claim 14 planted in an athletic field.

20. The grass plant of claim 14 planted in a park.

21. A method of producing grass seed, comprising
 (a) planting grass seed according to claim 9 under conditions that result in the germination of the seed, growth of grass plants and setting of progeny seed; and
 (b) harvesting the progeny seed.

22. Grass seed produced by the method of claim 21.

23. A mixture of grass seed comprising the grass seed of claim 22.

24. A method of producing a grass plant, the method comprising:
 (a) crossing a first grass plant with at least one other grass plant to produce at least one seed, wherein the first grass plant is a grass plant according to claim 1;
 (b) harvesting the seed; and
 (c) germinating the seed to produce at least one progeny grass plant.

25. A grass plant produced by the method of claim 24.

26. Sod, comprising the grass plant of claim 25.

27. The grass plant of claim 25 planted in a golf course fairway.

28. The grass plant of claim 25 planted in a golf course rough.

29. The grass plant of claim 25 planted in a lawn.

30. The grass plant of claim 25 planted in an athletic field.

31. The grass plant of claim 25 planted in a park.

32. A vegetative sprig or clone of the grass plant of claim 25.

33. The grass plant of claim 25, further comprising at least one transgene.

* * * * *

UNITED STATES PATENT AND TRADEMARK OFFICE
CERTIFICATE OF CORRECTION

PATENT NO.    : 6,372,966 B1
DATED         : April 16, 2002
INVENTOR(S)   : Rose-Fricker et al.

It is certified that error appears in the above-identified patent and that said Letters Patent is hereby corrected as shown below:

Column 6,
Table 11, "#1 HyPure Gel" and "#2 HyPure Gel" should read
-- EST #1 HyPure Gel -- and -- EST #2 HyPure Gel --.

Signed and Sealed this

Twenty-eighth Day of January, 2003

JAMES E. ROGAN
*Director of the United States Patent and Trademark Office*